United States Patent [19]

Cottingham

[11] Patent Number: 4,806,015
[45] Date of Patent: Feb. 21, 1989

[54] AGGLUTINATION DETECTION APPARATUS

[76] Inventor: Hugh V. Cottingham, 49 Mountain Ave., Caldwell, N.J. 07006

[21] Appl. No.: 130,717

[22] Filed: Dec. 8, 1987

[51] Int. Cl.$^4$ .................... C01N 15/02; C01N 21/59; C01N 21/82
[52] U.S. Cl. ................................. 356/335; 356/442; 422/73
[58] Field of Search .................. 356/37, 38, 39, 335, 356/441, 442, 244; 422/73

[56] References Cited

U.S. PATENT DOCUMENTS

| | | | |
|---|---|---|---|
| 3,503,684 | 3/1970 | Preston, Jr. et al. | 356/39 |
| 3,676,647 | 7/1972 | Staffin et al. | 377/11 |
| 4,547,075 | 10/1985 | Fei | 356/442 X |

FOREIGN PATENT DOCUMENTS 1173263  8/1985  U.S.S.R. .............................. 356/335

Primary Examiner—Davis L. Willis
Assistant Examiner—Matthew W. Koren
Attorney, Agent, or Firm—Blum Kaplan

[57] ABSTRACT

A detection system for detecting the degree of agglutination of particles in an agglutination reaction occurring in a test slide having a display area of a predetermined length and thickness is provided. A laser directs a diffraction limited spot at the display area of a test slide at intervals along the length of the display area. A photodetector detects the level of light attenuated by the particles and produces a detection signal representative of the size and number of particles scanned along the length of the display area by the laser light.

8 Claims, 10 Drawing Sheets

AGGLUTINATION DETECTION APPARATUS

BACKGROUND OF THE INVENTION

This invention is directed to a detection system for detecting the results of agglutination particle reactions produced within a diagnostic test slide and, in particular, to a detection system utilizing a laser scanner for detecting the occurrence of agglutination particle reactions within a diagnostic test slide.

A diagnostic test slide for effecting an agglutinographic reaction is described in U.S. application Ser. No. 932,067, entitled AGGLUTINOGRAPHIC SLIDE, filed in the name of the inventor herein, Hugh V. Cottingham, (hereinafter "the Cottingham test slide"). The Cottingham test slide causes an agglutination reaction to occur and causes the reaction to be displayed in a window display area. The presence or absence of an agglutination reaction is intended to be read by the human eye.

The disadvantage of using the Cottingham diagnostic test slide or, for that matter, any agglutination test that is read by the human eye is that the sensitivity of the reaction is limited by the ability of the human eye to resolve the differences between reacted and unreacted particles. As differences between the size of the reacted and unreacted particles becomes smaller, the error and subjectivity of a visual reading increases. Accordingly, an agglutinographic reaction detection system that utilizes a laser scanner in combination with a test slide to diagnostically detect the size and distribution of agglutinated particles is desired.

SUMMARY OF THE INVENTION

Generally speaking in accordance with the instant invention, an agglutination detection apparatus is provided for detecting agglutination of particles in a test slide having a display area of predetermined length and thickness and defining a gap. The detection apparatus includes a housing for positioning the test slide. A laser light source is disposed in the housing and focuses a light beam to define a diffraction limited spot in the gap. A photo detector disposed on the opposite side of the slide detects the level of light transmitted through the slide at the spot. The focused light beam is adapted to scan a path of spots across the slide so that the photodetector produces signals representative of measurements of transmitted light taken at predetermined distance intervals along the scanning path. The distance of each interval is selected to be a fraction of the diameter of the particles being scanned. A detector circuit is adapted to receive each signal produced by the photodetector and produce a signal representative of the size and the number of particles scanned.

Accordingly, it is an object of the instant invention to provide an improved agglutination detection system.

A further object of the instant invention is to provide an agglutination detection apparatus which is simple to use and does not depend for reading upon an individual's visual acuity.

Still another object of the instant invention is to provide a detection system which digitally detects the size and distribution of agglutinized particles.

Still a further object of the instant invention is to provide a laser scanning instrument for reading an agglutinographic slide and for producing a reading based upon the size and distribution of the particles scanned.

Still another object of the invention is to provide an agglutination detection apparatus which is capable of reading an agglutination reaction occurring in a test slide, is responsive to changes in particle size, is easy to use, and avoids passing contaminants from one sample to another.

Still other objects and advantages of the invention will in part be obvious and will be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a better understanding of the invention, reference is had to the following description taken in connection with the accompanying drawings, in which.

DETAILED DESCRIPTION OF THE PREFERRED EMBODIMENTS

Figure 1:
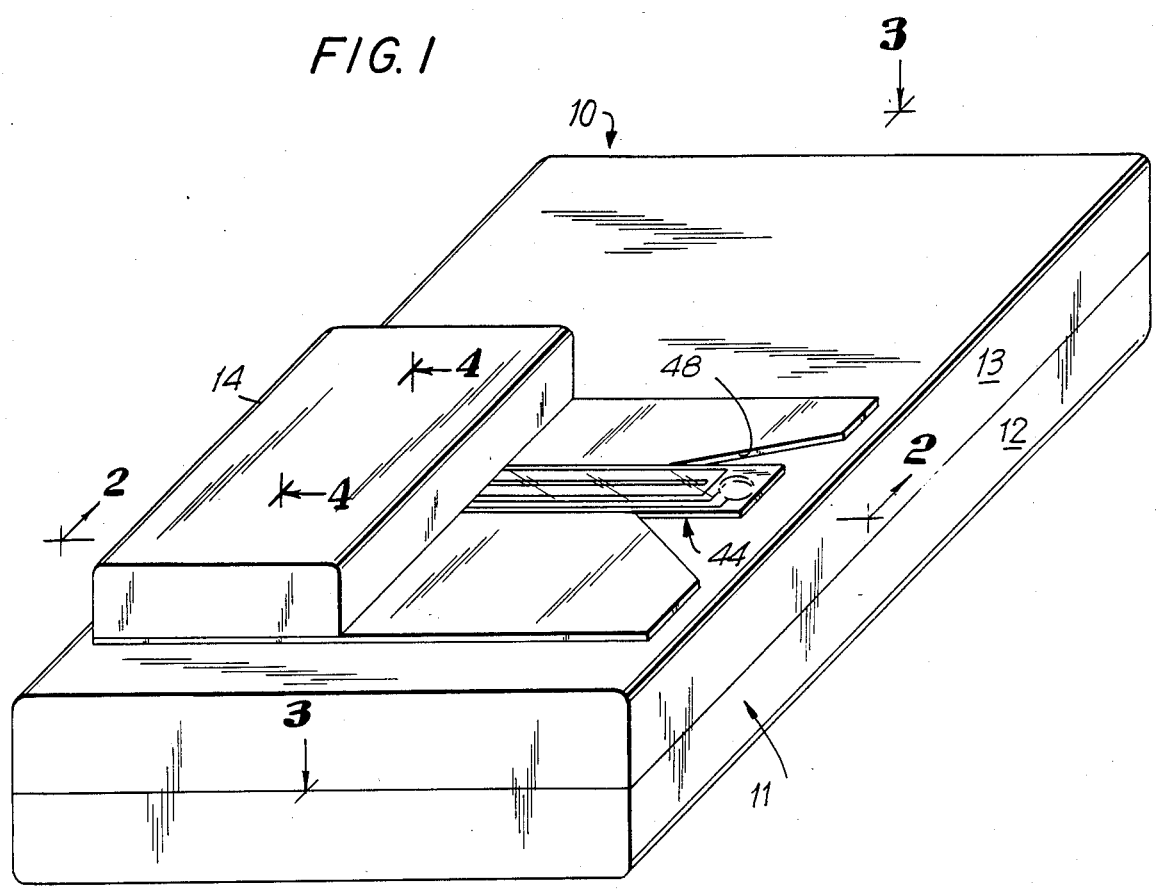
FIG. 1 is a perspective view of an agglutination detection instrument constructed in accordance with a preferred embodiment of the instant invention.

Reference is first made to FIGS. 1, 1b, 2, and 3 wherein an agglutination reagent detection instrument, generally indicated as 10, and constructed in accordance with a preferred embodiment of the instant invention, is depicted. Instrument 10 includes a housing, generally indicated as 11, including a base 12, cover 13, and a hood 14.

A pair of rods 20 are supported by housing 11 and extend in parallel. A moving carriage 22 is slideably mounted upon rods 20 so that carriage 22 can be displaced in a reciprocating manner, to be described in greater detail below.

A laser diode 24 is mounted on carriage 22, laser diode 24 emits a laser light 52 which is directed through diffraction optics, generally identified as 25, and includes a polarizer 26, a collimating lens 28, a reflecting prism 30 and an optical focusing assembly 32. Collimating lens 28 produces a collimated laser beam 52. Beam 52 is bent by reflecting prism 30 and passes through an optical focusing assembly 32. Focus assembly 32 converges the collimated laser beam into a diffraction limited spot within the agglutination slide 44. A photo detector 34 is mounted on carriage 22 in the optical path of the beam 52 produced by diode 24 at a position adjacent the electronic focusing assembly 32 and detects the laser light transmitted through slide 44.

Also mounted on carriage 22 is a gear rack 36. A gear train 38 is supported on platform 37 and is mechanically coupled to gear rack 36. A dual direction motor 40 drives gear train 38 so that carriage 22 is displaced in a reciprocating motion along the axis defined by arrows A in FIG. 3. A circuit board 42 is supported on frame 18 and controls the operation of photo diode detector 34 and laser diode 24. Flexible wires 58 connect detector 34 to circuit board 42, while flexible wires 60 connect laser diode 24 to circuit board 42. Circuit board 42, as will be explained below, determines when the output of detector 34 corresponds to an agglutination and will indicate such a result to the operator through means such as a electronic display 59 or printout (not shown).

Figure 1A:
FIG. 1a is a perspective view of an agglutinographic reagent test slide for use in the detector of FIG. 1.
Figure 1B:
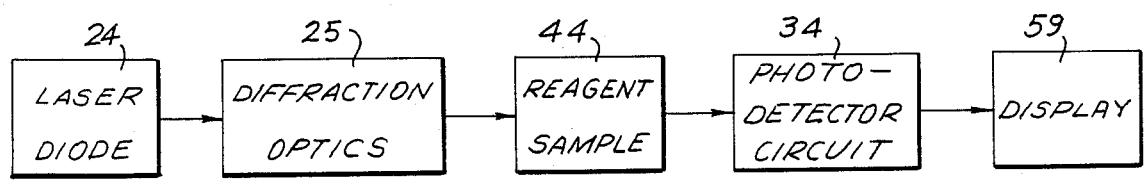
FIG. 1b is a block diagram illustrating an electro-optical representation of the laser instrument depicted in FIG. 1.
Figure 2:
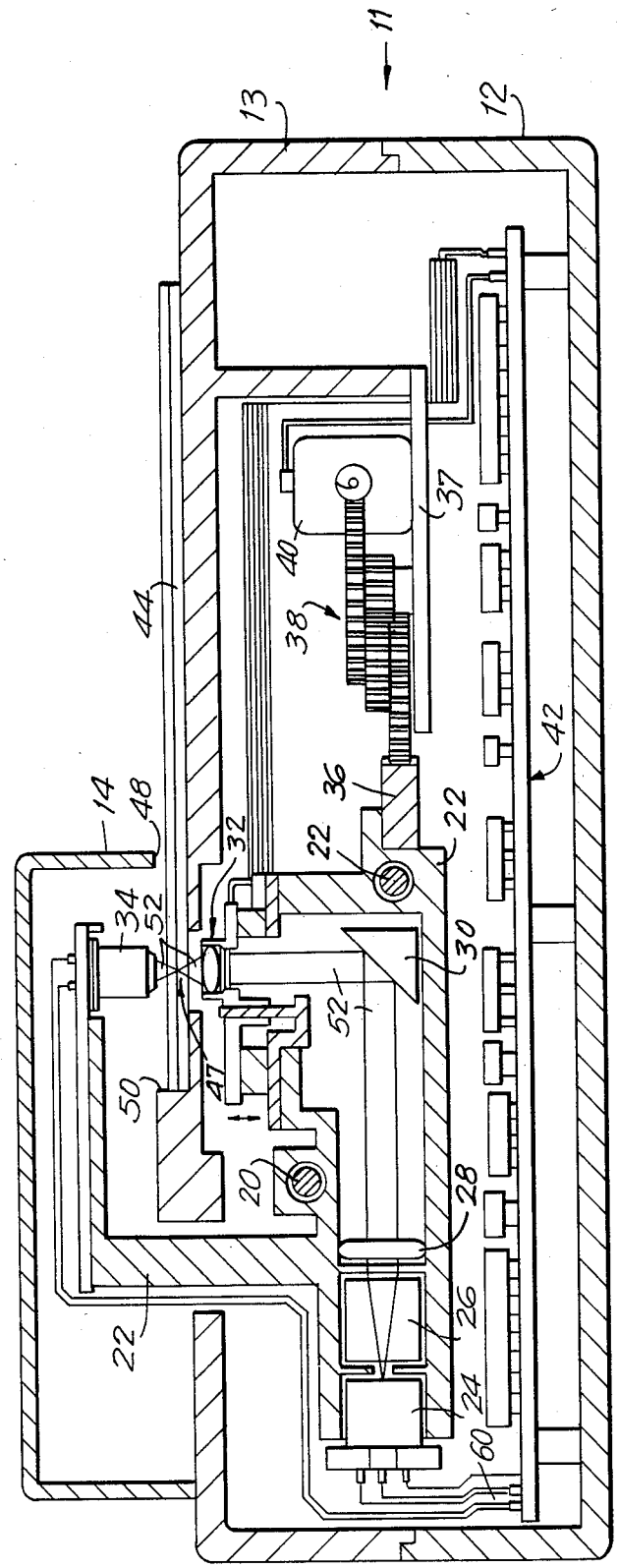
FIG. 2 is a sectional view taken along the line 2—2 of FIG. 1.
Figure 3:
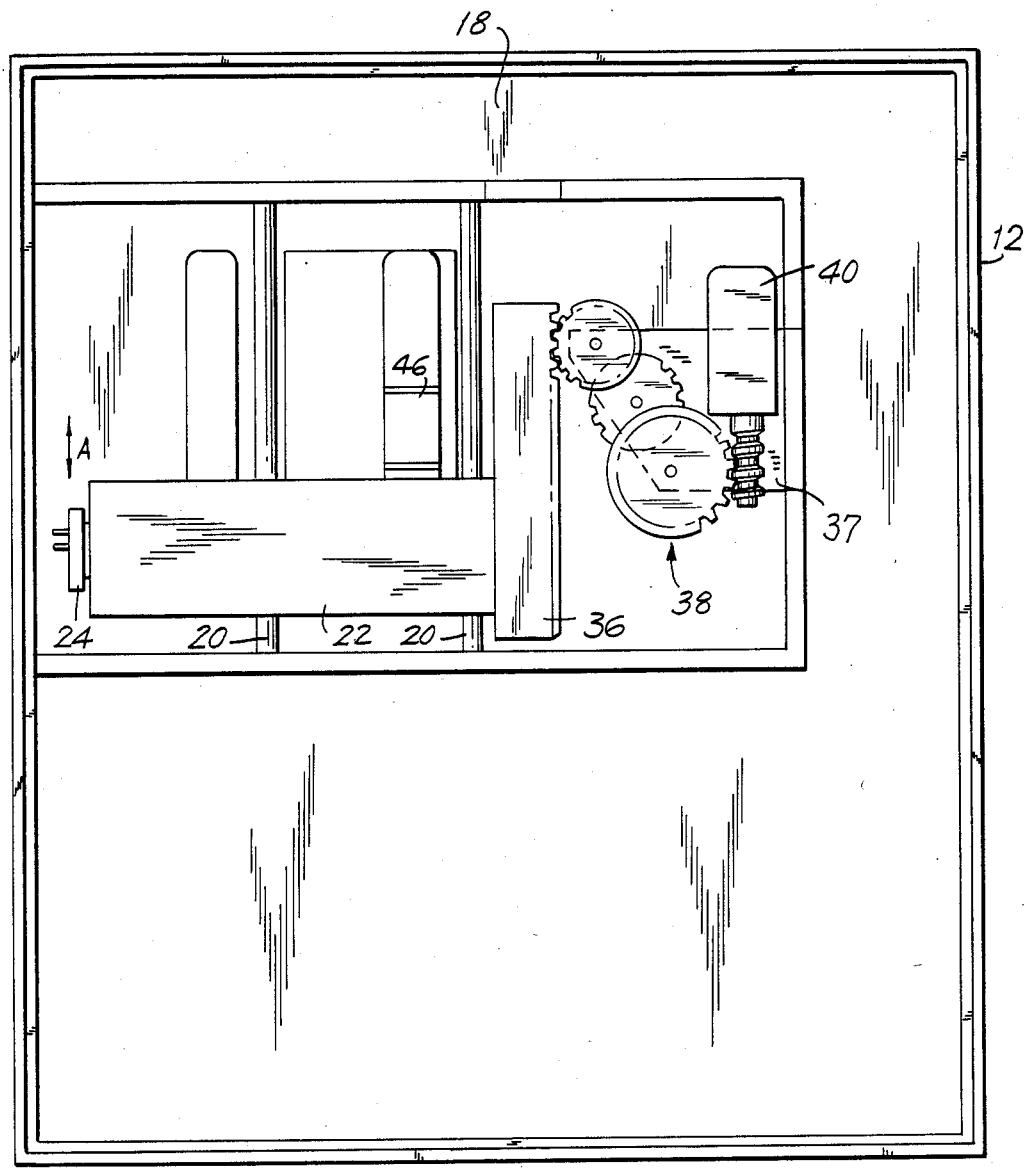
FIG. 3 is a sectional view taken along line 3—3 of FIG. 1.
Figure 4:
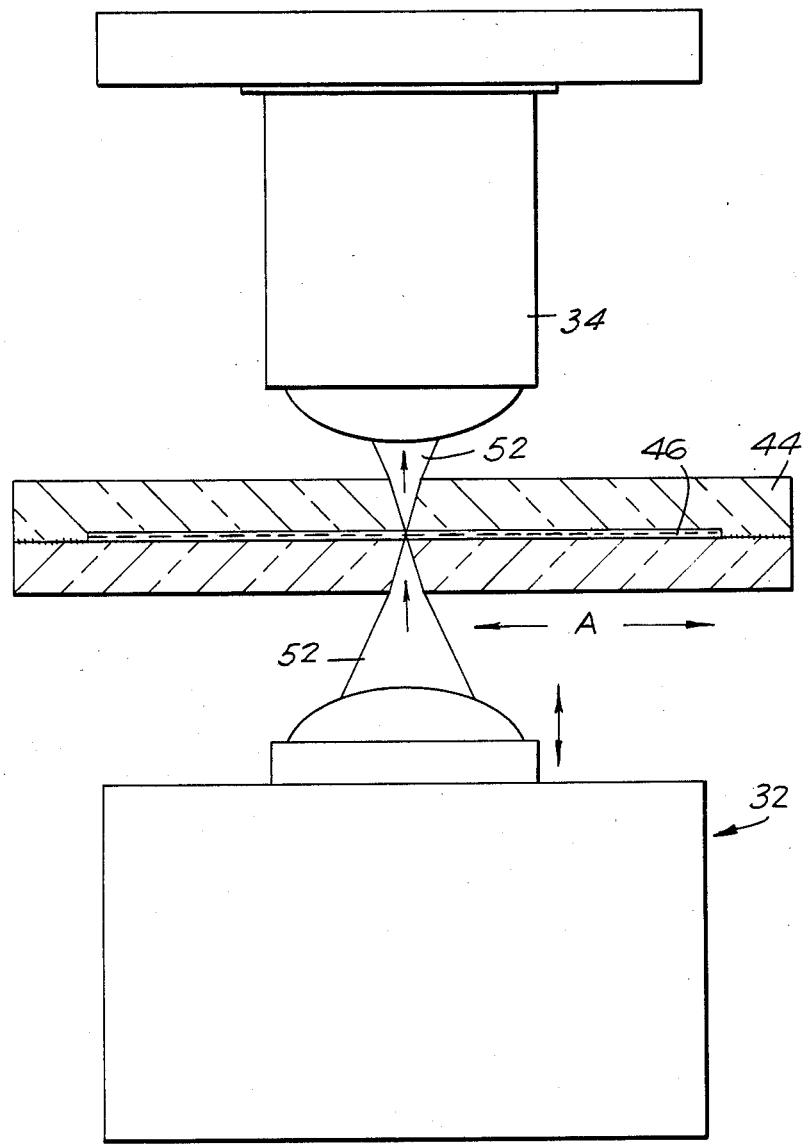
FIG. 4 is an enlarged sectional view taken along line 4—4 of FIG. 1.
Figure 5:
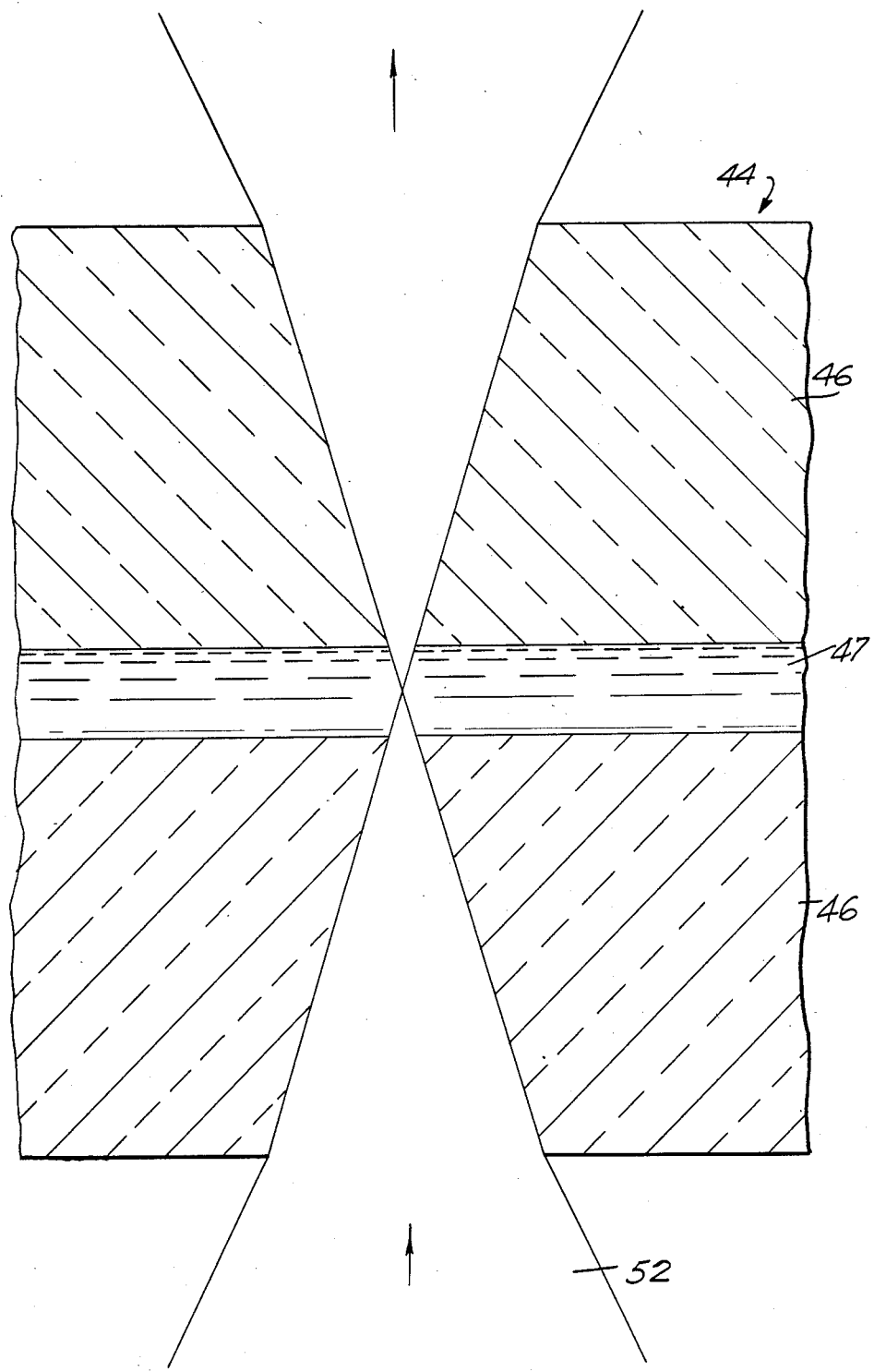
FIG. 5 is an enlarged view of FIG. 4.
Figure 6:
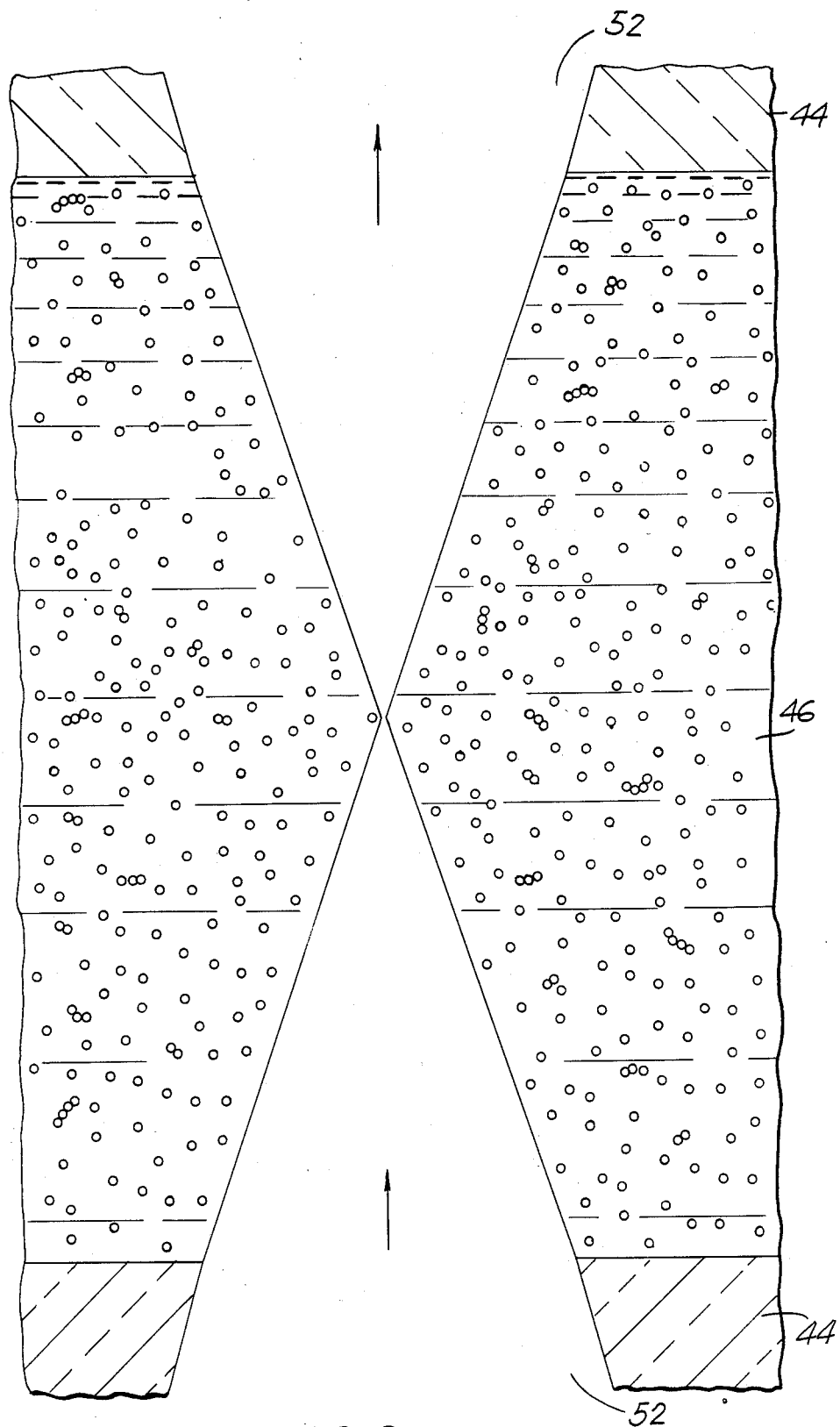
FIG. 6 is an enlarged view of FIG. 5 showing a beam of laser light passing through a suspension of monomeric particles.

Cottingham test slide 44 (FIG. 1a) causes an agglutination reaction to occur in a window area 46. Cottingham test slide 44 is placed in the instrument through a slot 48 defined by a clearance between hood 14 and cover 13. In a preferred embodiment, a slide of the type described in U.S. application No. 932,067 is preferred and, accordingly, the disclosure of U.S. application No. 932,067 is incorporated by reference as if fully set forth herein. However, any slide and reagent wherein the combination of the geometry of the test slide and the type of agglutination particle reagents that will provide a combined optical density, referred to herein as a 'gap', that does not fully attenuate the laser beam can be utilized with instrument 10. For example, for a test slide having a sample 150$\mu$ thick, a 0.1 to 0.5%, latex by weight agglutination reagent can be utilized.

When Cottingham test slide 44 is displaced into the slot, the housing cover is configured so that the slide is positioned against a stop 50, disposed within hood 14. Stop 50 indexes Cottingham test slide 44 relative to light beam 52 of diode 24.

As discussed above, collimated beam 52 emerges from electronic focus assembly 32, as a converging beam, which is accurately focused as a diffraction limited spot within gap 47 of the slide. Beam 52 is focused to the diffraction limited spot which is about one micron in diameter at a point within the liquid particle suspension contained in window 46. Laser beam 52 passes through slide 44, diverges and then impinges on photo diode detector 34. Photo diode 34 produces a detection signal having a voltage level representative of the amount of impinging light detected by the photo diode. The detection signal is then processed by circuit 42 and applied to a display 59.

As beam 52 is focused at the slide, motor 40 drives gear train 38 to cause carriage 22 to move in a line across slide 44 tracing a scanning path in the direction of arrow A, hence, allowing laser diode 24 and photo detector 34 to scan across window 46. During this first pass across slide 44, focus assembly 32 is continuously being adjusted to scan at a plurality of different focus levels as carriage 22 proceeds along the first path. Once the first path has been completed, the optimal focus within gap 47 is determined from each of the focus positions of the first scan. Motor 40 is then reversed in direction to perform a second scan in which laser 24 and photo diode detector 34 rescans the slide to collect data. At the end of this second pass, carriage 22 is returned to its starting point.

Reference is now also made to FIGS. 4 through 9 in which the action of the beam as it passes through window 46 is illustrated in greater detail. As discussed above, beam 52 converges as it enters slide 44 and diverges as it exits slide 44. The beam converges to a spot approximately the size of a single particle of a non-agglutinating (monomeric) sample. In the present example the size of a monomeric particle is 0.8 $\mu$m. The voltage output of the detector is sampled each time carriage 22 traverses a predetermined distance. The distance is a small fraction of the actual size of a monomeric particle. In a preferred embodiment, the voltage output detector is sampled every 155 nanometers of the linear scan distance to obtain size information. In the present system a 1 $\mu$m diameter particle will be measured at 6 points as the laser beam 52 scans across the particle.

Figures 8A, 8B, 8C, 8D, 8E:
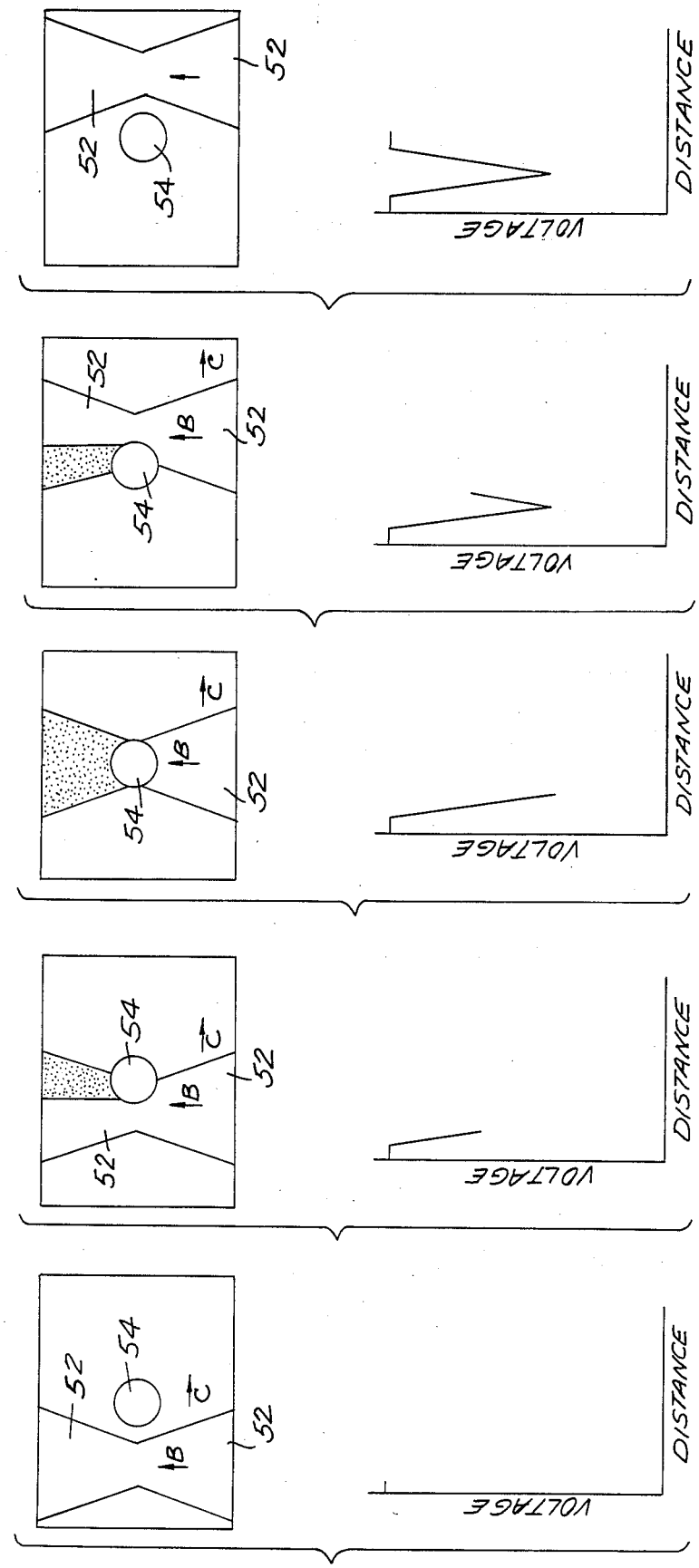
FIGS. 8a-8e graphically illustrate the beam-particle interaction and change in output of the photodetector which occurs as a particle is scanned.

The process is best illusrated in FIG. 8, wherein laser beam 52 passes across monomeric particle 54. Laser beam 52 is directed in the direction of arrow B and, as it scans the slide, travels in the direction of arrow C. Scanning laser beam 52 has a nominal transmission level which is detected as a certain voltage level by photo diode detector 34 (FIG. 8a). As light beam 52 becomes partially attenuated by particle 54 in the light path, the voltage detected by photo detector 34 begins to decrease (FIG. 8b) until reaching a maximum attenuation point which represents the bottom of a voltage graph (FIG. 8c). As particle 54 leaves the path of laser light beam 52, light beam 52 becomes less attenuated (FIG. 8d) and returns to the nominal voltage level of a totally unblocked light beam 52 (FIG. 8e).

As mentioned above, the voltage output of detector 34 is sampled every 155 nanometers of the linear scan distance of the laser beam. Accordingly, it becomes possible to acurately measure the size of the particle by calculating the distance travelled by beam 52 between successive readings of the nominal voltage level. Furthermore, since the typical particle is measured at a number of points, the system has inherently high resolution. Therefore, agglutination may be detected when the size and number of particles detected differ from the size and number (distribution) expected for the particular particle being studied. Therefore, agglutinations can be determined even when the reaction is at such an early stage that only two particles are joined.

Figure 9:
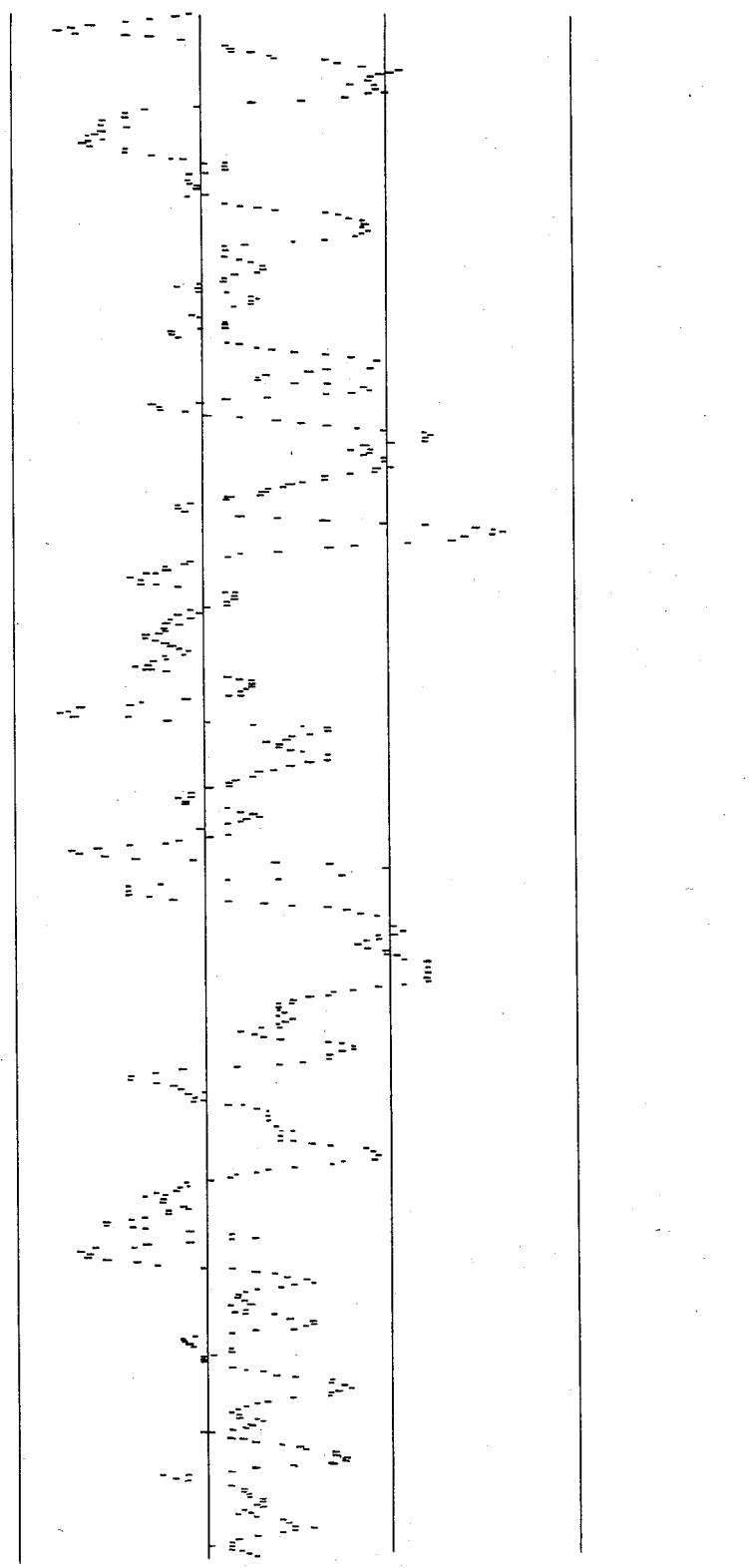
FIG. 9 is a graph showing an actual segment of data points of a monomeric sample as it is scanned.
Figure 10:
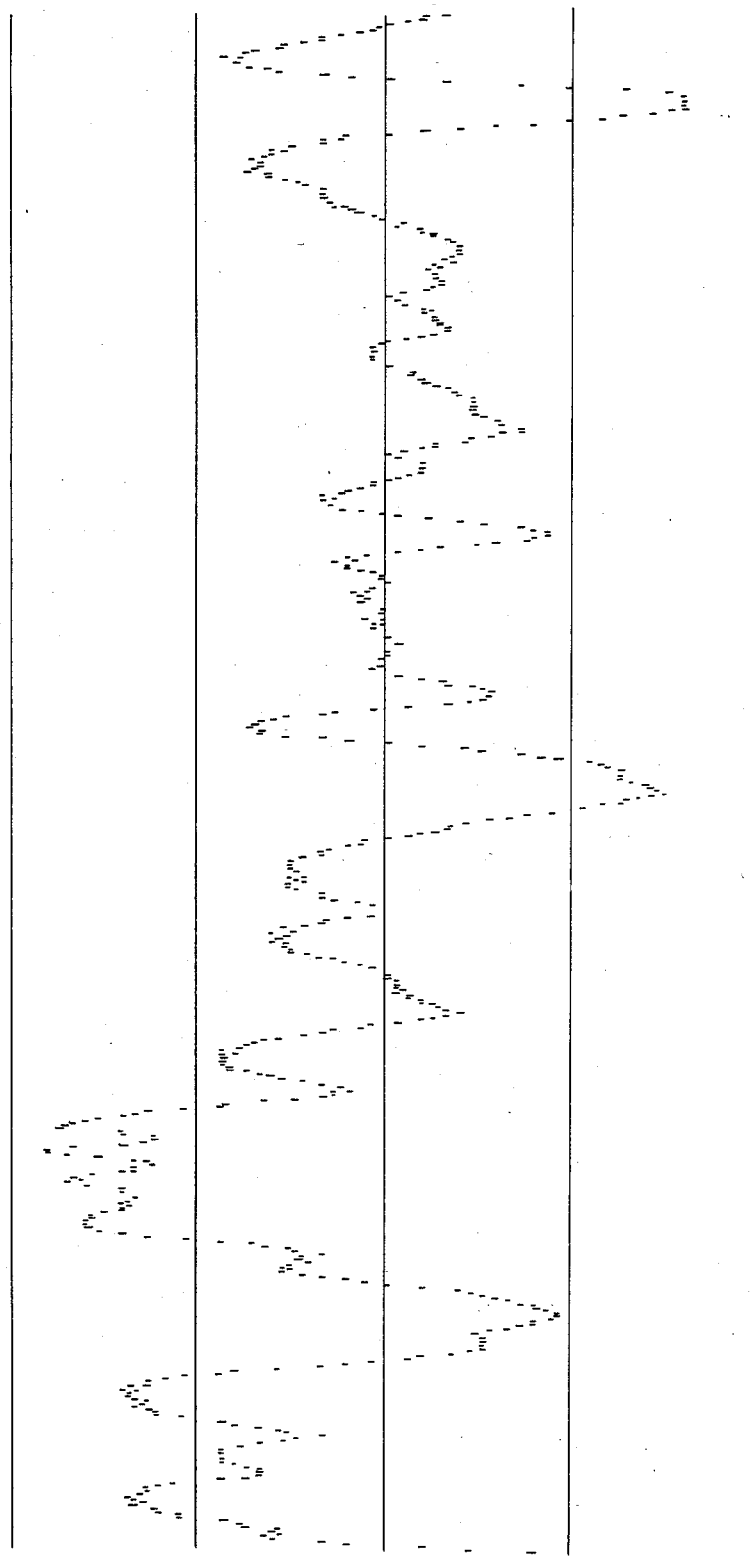
FIG. 10 is a graph showing a segment of actual data points of a sample of agglutinated particles as it is scanned.

Actual operation of agglutination detector 10 is shown with actual data in Tables 1 and 2 and FIGS. 9 and 10. FIG. 9 is a plot of actual data across a 100 micron section of a 1 centimeter scan across window 46. The points along the graph represent the detector output voltage as measured every 155 nanometers of the scan. Each peak in the graph represents a particle being scanned by the laser beam, i.e. attenuation. FIG. 9 is data from a monomeric sample (1/100th of the data) of the type depicted in FIG. 6. Table 1 provides a summary of the number of particles equalling the size of each channel and the number of particles detected at each channel size, when each channel equals 155 nanometers.

TABLE 1

| MONOMERIC SAMPLE | | | | | | | |
|---|---|---|---|---|---|---|---|
| chan | +0 | 21 | 41 | 61 | 101 | 141 | 181 | 221 |
| 1 | — | 17 | — | — | — | — | — | — |
| 2 | — | 5 | — | 1 | — | — | — | — |
| 3 | — | 8 | — | — | — | — | — | — |
| 4 | — | 13 | 2 | — | — | — | — | — |
| 5 | 2 | 9 | — | — | — | — | — | — |
| 6 | 23 | 7 | — | — | — | — | — | — |
| 7 | 100 | 6 | — | — | — | — | — | — |
| 8 | 145 | — | — | — | — | — | — | — |
| 9 | 150 | 3 | 1 | — | — | — | — | — |
| 10 | 120 | 3 | — | — | — | — | — | — |
| 11 | 98 | 1 | — | — | — | — | — | — |
| 12 | 57 | 2 | — | — | — | — | — | — |
| 13 | 53 | 2 | — | — | — | — | — | — |
| 14 | 41 | — | — | — | — | — | — | — |
| 15 | 31 | 2 | — | — | — | — | — | — |
| 16 | 21 | — | — | — | — | — | — | — |
| 17 | 19 | — | — | — | — | — | — | — |
| 18 | 17 | — | — | — | — | — | — | — |
| 19 | 22 | — | — | — | — | — | — | — |
| 20 | 17 | — | — | — | — | — | — | — |

As is expected in a monomeric field, when the average size of each particle is 0.8 microns the majority of the particles have a size between six channels and 12 channels. This is illustrated by Table 1 and the large number of particles identified around the expected average size. Such a table may be printed out by detector 16 to indicate the extent of agglutination or non agglutination.

Figure 7:
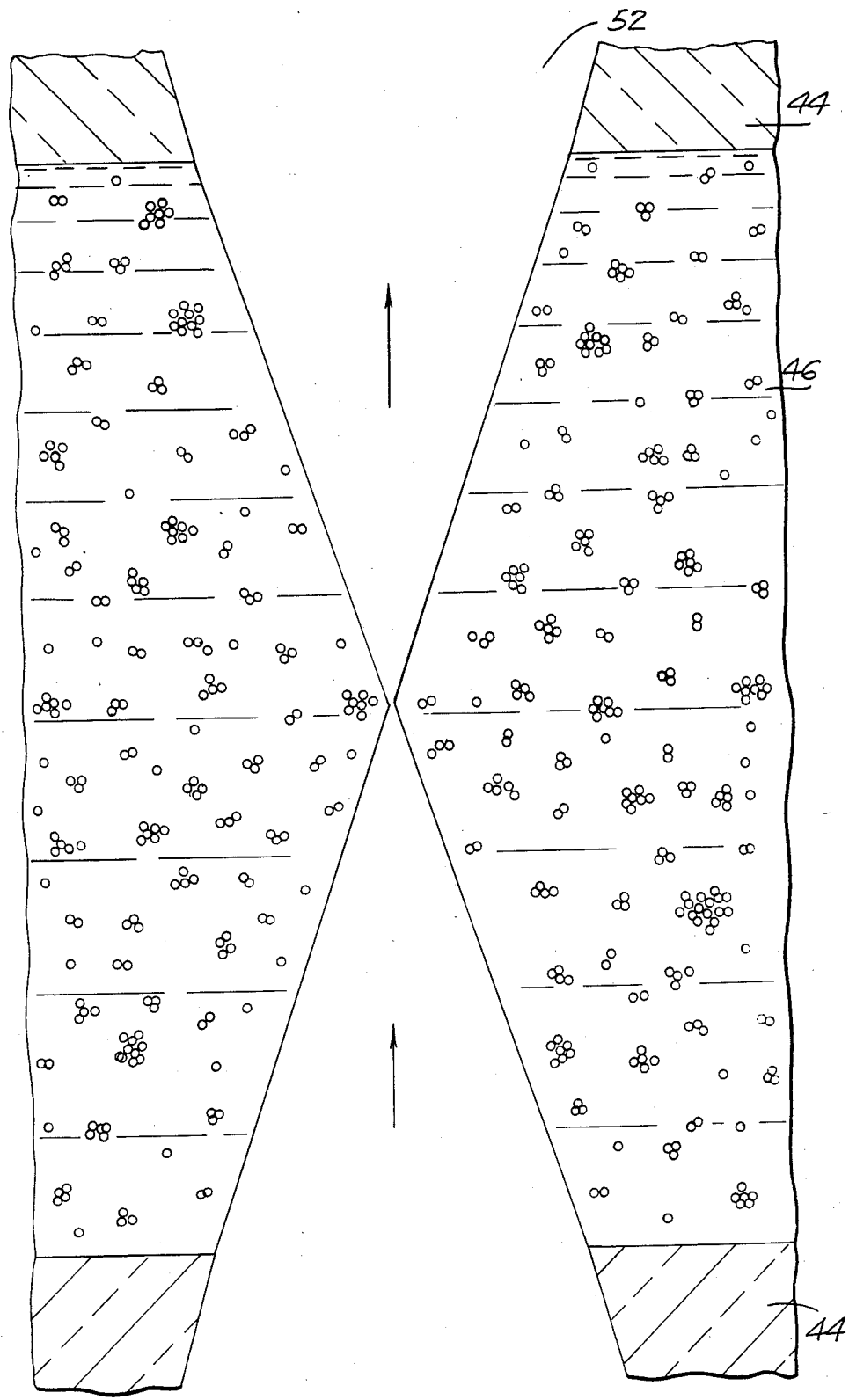
FIG. 7 is an enlarged view of FIG. 5 showing a beam of laser light passing through a suspension of agglutinated particles.

However, if this result is compared with detection readings taken from a sample such as that of FIG. 7 where agglutination has occurred, a totally different type of array occurs

TABLE 2

| AGGLUTINATION SAMPLE | | | | | | | |
|---|---|---|---|---|---|---|---|
| chan | +0 | 21 | 41 | 61 | 101 | 141 | 181 | 221 |
| 1 | — | 16 | 5 | 1 | — | — | — | — |
| 2 | — | 16 | 2 | — | — | — | — | — |
| 3 | — | 15 | 1 | — | — | — | — | — |
| 4 | — | 7 | 2 | — | — | — | — | — |
| 5 | 3 | 13 | 5 | — | — | — | — | — |
| 6 | 8 | 6 | — | — | — | — | — | — |
| 7 | 33 | 6 | 1 | — | — | — | — | — |
| 8 | 29 | 11 | — | — | — | — | — | — |
| 9 | 46 | 11 | 1 | 1 | — | — | — | — |
| 10 | 34 | 6 | 1 | — | — | — | — | — |
| 11 | 40 | 4 | 1 | — | — | — | — | — |
| 12 | 37 | 4 | 2 | — | 1 | — | — | — |
| 13 | 38 | 4 | 2 | — | — | — | — | — |
| 14 | 29 | 3 | — | 1 | — | — | — | — |
| 15 | 22 | 2 | — | 1 | 1 | — | — | — |
| 16 | 35 | 2 | — | — | — | — | — | — |
| 17 | 21 | 1 | — | — | — | — | — | — |
| 18 | 21 | 1 | — | — | — | — | — | — |
| 19 | 20 | 1 | 2 | — | — | — | — | — |
| 20 | 26 | 3 | — | — | — | — | — | — |

As expected, the size and distribution of particles or agglutinations has a higher number of larger sizes occurring in contrast to the higher numbers of smaller sized particles occurring in the monomeric data table. This is also reflected in the general shape of the voltage peaks illustrated IN FIG. 9 and FIG. 10.

Accordingly, it is possible to detect, based upon this type of data, when agglutinations have occurred. Due to the high resolution of the agglutination detecting instrument 10, reactions at a point of reaction where only dimeric agglutination has occurred, well before the point detectable by the human eye can be detected. Furthermore, by generating size and distribution data from the scan, the laser detection system can utilize more than one parameter to provide more accurate readings.

By providing a laser detector which passes a laser light beam through an agglutinographic test sample, wherein the light beam is roughly the size of an expected monomeric particle and the output from a light detector is sampled at distances a fraction of the diameter of the monomeric sample, an agglutination detector having high resolution is provided.

It will thus be seen that the objects set forth above and those made apparent in the preceding description, are efficiently attained and, since certain changes may be made in the above construction without departing from the spirit and scope of the invention it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. In an apparatus for detecting the degree of agglutination of particles in an agglutination reaction in a test slide having a display area of predetermined length and thickness, said thickness defining a gap; the improvement comprising a light source means for directing a diffraction limited spot at said gap at predetermined distance intervals along the length of the display area, and detection means for detecting the level of light attenuated by particles in said gap, and for producing a detector signal representative of the size and number of particles scanned.

2. The detection apparatus, as claimed in claim 1, wherein the light source means directs a diffraction limited spot having a size on the order of the diameter of a single particle.

3. The detection apparatus, as claimed in claim 1, and further including display means for receiving said detection signal from said detection means and providing a display representative of the degree of agglutination of the particles in the reagent.

4. The detection apparatus, as claimed in claim 1, wherein each predetermined distance interval is less than 20% of the diameter of said particle.

5. The detection apparatus, as claimed in claim 2, wherein said predetermined distance interval is less than 20% of the diameter of said particle.

6. The detection apparatus, as claimed in claim 1, wherein said light source means includes a laser diode.

7. The detection apparatus, as claimed in claim 1, wherein the detection means includes a photo detector diode.

8. The detection apparatus, as claimed in claim 7, wherein the detection means is a photodetector diode.

* * * * *